(12) United States Patent
Levi

(10) Patent No.: US 9,707,060 B1
(45) Date of Patent: Jul. 18, 2017

(54) METHOD OF RESTORING ANTERIOR ENDODONTICALLY TREATED TEETH

(71) Applicant: Jack Levi, Teaneck, NJ (US)

(72) Inventor: Jack Levi, Teaneck, NJ (US)

(*) Notice: Subject to any disclaimer, the term of this patent is extended or adjusted under 35 U.S.C. 154(b) by 0 days.

(21) Appl. No.: 14/569,922

(22) Filed: Dec. 15, 2014

Related U.S. Application Data

(63) Continuation-in-part of application No. 13/329,717, filed on Dec. 19, 2011, now abandoned.

(51) Int. Cl.
*A61C 5/02* (2006.01)
*A61C 13/08* (2006.01)
*A61C 9/00* (2006.01)
*A61C 5/08* (2006.01)
*A61C 5/04* (2006.01)

(52) U.S. Cl.
CPC .............. *A61C 13/082* (2013.01); *A61C 5/04* (2013.01); *A61C 5/08* (2013.01); *A61C 9/004* (2013.01)

(58) Field of Classification Search
CPC .. A61C 5/02; A61C 5/04; A61C 5/023; A61C 5/045
USPC .................................................. 433/224–226
See application file for complete search history.

(56) References Cited

U.S. PATENT DOCUMENTS

| | | | | |
|---|---|---|---|---|
| 4,936,776 A | * | 6/1990 | Kwiatkowski | A61C 5/04 433/220 |
| 5,403,187 A | * | 4/1995 | Wauchope | A61C 5/00 433/166 |
| 5,639,239 A | * | 6/1997 | Earle | A61C 5/08 433/218 |
| 5,897,316 A | * | 4/1999 | Buchanan | A61O 5/023 433/102 |
| 5,964,592 A | * | 10/1999 | Hites | A61C 13/30 433/221 |
| 7,086,864 B2 | * | 8/2006 | Lopez | A61C 13/30 433/224 |
| 2005/0227204 A1 | * | 10/2005 | Hauck | A61C 13/0001 433/218 |
| 2006/0154207 A1 | * | 7/2006 | Kuo | A61C 13/0003 433/202.1 |

(Continued)

OTHER PUBLICATIONS

Reddy et al. (Management of transverse root fracture by dowel-inlay; A case report, Journal of International Oral Health, Feb. 2011; vol. 3 issue 1) in view of Baratieri et al. (Influence of post placement in the fracture resistance of endodontically treated incisors veneered with direct composite, The Journal of Prosthetic Dentistry, Volume.*

(Continued)

*Primary Examiner* — Cris L Rodriguez
*Assistant Examiner* — Matthew Saunders

(57) ABSTRACT

Endodontically treated teeth can be restored with porcelain facial veneer restorations-layering ceramic and porcelains. The method includes the steps of providing a cement material for preventing microleakage into gutta percha and for forming a post-barrier space. A rhomboid access inlay-shaped porcelain core is provided with an anatomical post extension extending below a level of an existing crest of bone into a root canal space, the length of the post extension being less than one-half the length of a root canal. The modified post is seated into a post barrier cement to prevent the egress of moisture or bacterial microleakage to the apex of the root canal.

16 Claims, 5 Drawing Sheets

(56) References Cited

U.S. PATENT DOCUMENTS

2008/0206715 A1* 8/2008 Kawamoto ............. A61C 3/02
                                                    433/226
2012/0100507 A1* 4/2012 Olson ................... A61O 5/125
                                                    433/217.1
2015/0030996 A1* 1/2015 Hernandez ........... A61C 13/082
                                                    433/203.1

OTHER PUBLICATIONS

Baratieri et al. (Influence of post placement in the fracture resistance of endodontically treated incisors veneered with direct composite, The Journal of Prosthetic Dentistry, vol. 84, Issue 2, Aug. 2000, pp. 180-184).*

Grande et al. ( Adapting fiber-reinforced composite root canal posts for use in noncircular-shaped canals. Practical Procedures in Aesthetic Dentistry, Oct. 2006;18(9):593-9).*

* cited by examiner

FIG. 1
FIG. 2
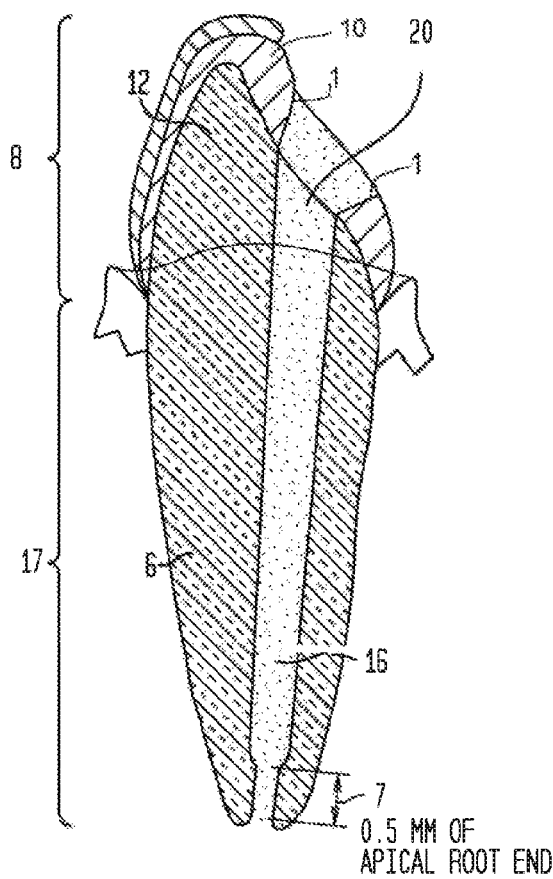
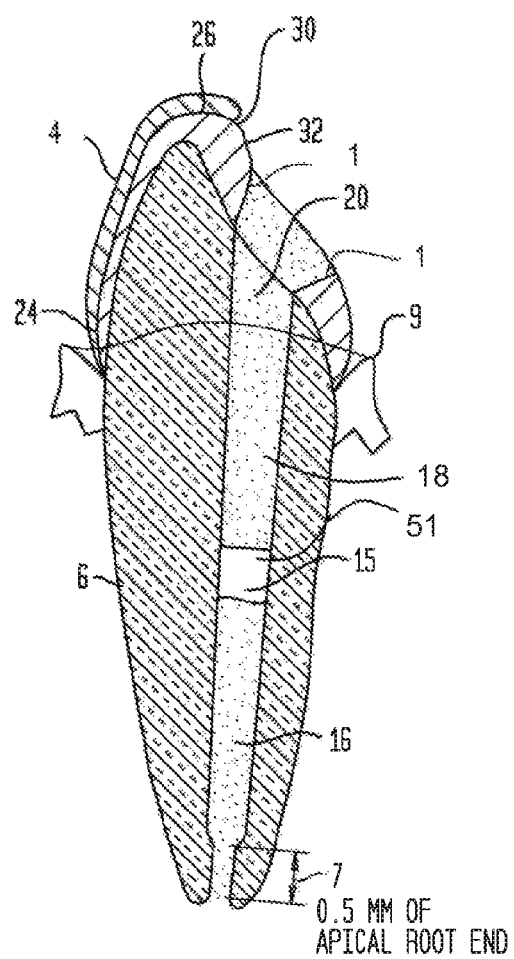

FIG. 6
FIG. 7
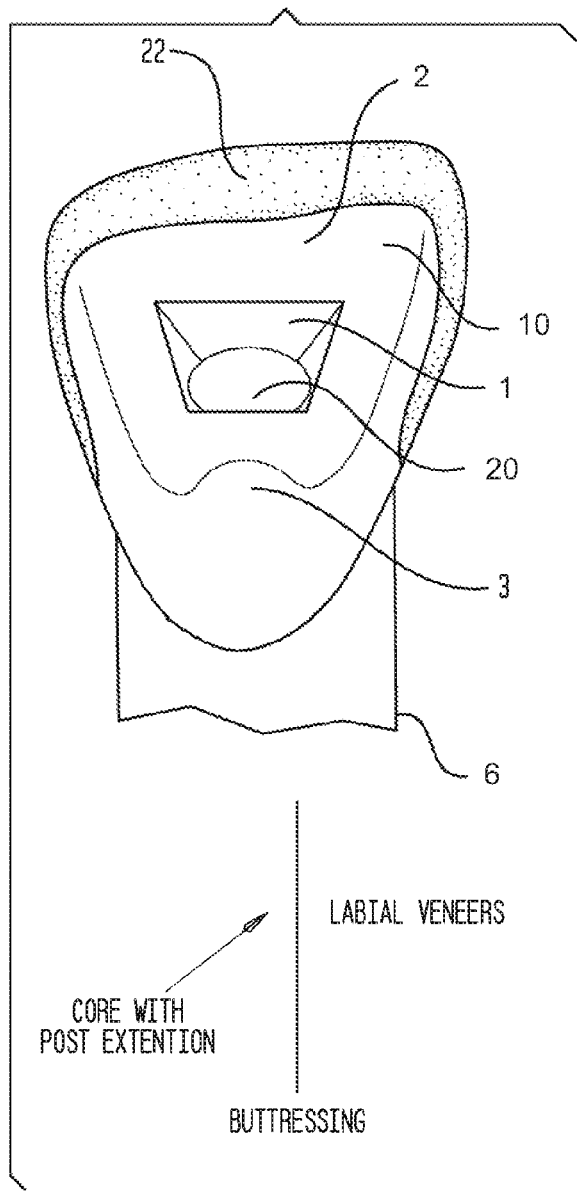
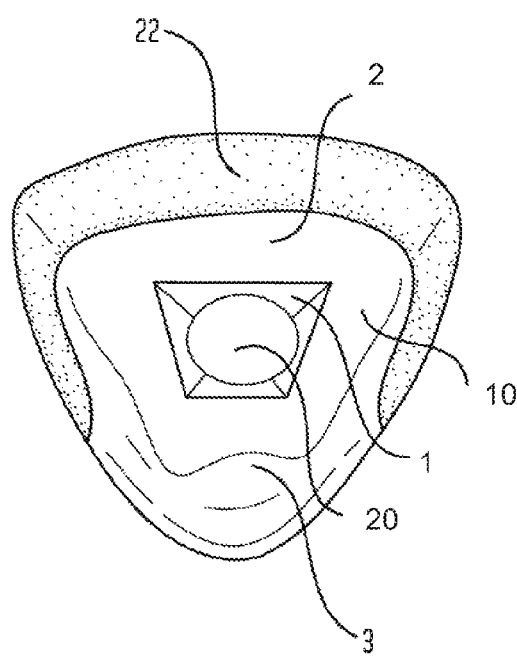

METHOD OF RESTORING ANTERIOR ENDODONTICALLY TREATED TEETH

CROSS-REFERENCE TO RELATED APPLICATIONS

The present application is a continuation application of patent application Ser. No. 13/329,717, for Restoration Of Anterior Endodontically Treated Teeth, filed Dec. 19, 2011, and U.S. Provisional Patent No. 61/425,022, filed Dec. 20, 2010, and hereby incorporates the teaching therein by reference.

FIELD OF THE INVENTION

The disclosed subject matter relates to endodontics and, more particularly, to a method of restoring endodontically treated teeth, with porcelain facial veneer restorations.

BACKGROUND OF THE INVENTION

Endodontics or root canal therapy is that branch of dentistry that deals with the diseases of the dental pulp and periradicular tissues. One aspect of endodontics comprises the treatment of infected root canals by the removal of diseased pulp tissues, using biomechanical cleaning and shaping and subsequent filling of the pulp cavity (root canal). The access opening to the root canal must be sealed and the tooth restored. The objective in root canal therapy is to prevent leakage of toxic products from the coronal part of the tooth into the root canal system. The placement of a barrier material under the modified post assists in accomplishing this goal.

Root canal therapy is generally indicated for teeth having sound external structures but having diseased, dead, or dying pulp tissues. In such teeth, the pulp tissue and excised portions of the root should be replaced by a biocompatible substitute. The gold standard for filling the root canal is gutta percha and root canal sealer. Micro-leakage from the coronal portion of the tooth can pass through the gutta percha, filling to the apical portion to cause an abscess to form.

One technique for the preparation of a root canal involves creating a coronal straight line access opening with a conventional dental drill. The access opening in this technique is in the shape of a rhomboid inlay preparation, in the lingual surface of the anterior tooth. This facilitates the pattern withdrawal of the orifice seal and the connected modified post extension. In posterior teeth the access preparation is made through the occlusal tooth surface. A round bur is used for gross removal of pulp material from the pulp chamber through the coronal access opening. The canal orifices are located irrigated with sodium hypochlorite solution. The canals are negotiated with narrow files to establish the glide path of the canal. These files are rotated using a balanced force technique until free access to the foramen is reached. Apex locators are used to verify the length of the instrumented canal to the apex. Hand files are used to size #20, and then followed with nickel titanium rotary systems. Debris is removed from the root canal by flushing and evacuation after each instrument use. The root canals are cleansed of all diseased tissue and pulpal remnants. Following chemical antisepsis, the instrumented canal is ready for filling.

Current techniques typically fill the root canal with gutta percha, sealer, or resin. If posts are used, they are either active or passive, metal or fiber. A cosmetic and functional crown made of porcelain fused to metal is usually attached to the post and core. The placement of metal posts can result in perforations or fractures which may contribute to later tooth damage. Porcelain fused to metal crowns often show a dark unaesthetic hue at the cervical margin between the tooth and gingiva.

DESCRIPTION OF RELATED ART

U.S. Pat. No. 4,936,776 issued to Kwiatkoski, et al. for DENTAL PRODUCT AND METHOD UTILIZING TRANSLUCENT MATERIAL issued on Jun. 26, 1990 discloses a dental product and method utilizing pre-fabricated and fabricated translucent construct (e.g., glass ionomer) as the post or post-and-core of a dental restoration. Kwiatkoski, et al. use only a facial post and core veneer.

U.S. Published Patent Application No. 2005/0227204 on an application applied for by Hauck, et al. for DAILY WEAR TEMPORARY DENTAL VENEERS published on Oct. 13, 2005 discloses a method for temporarily improving an individual's smile, without any alteration of the individual's teeth comprising providing the individual with a plurality of thin, cosmetically pleasing, reusable veneers, each veneer designed to cover one tooth, and also providing the individual with a non-toxic bonding agent, so that the individual can personally attach a veneer to the front of a number of the individual's teeth by applying a thin layer of the bonding agent to a tooth or to the veneer, and pressing the veneer onto the tooth.

"Adapting Fiber-Reinforced Composite Root Canal Posts for Use in Noncircular-Shape Canals," by Grande, et al. in Practical Procedures in Aesthetics and Dentistry, 2006; 18(8):A-G describes a technique that adapts a preformed post to fit a noncircular-shaped root canal, starting from a commercially-available, preformed, fiber-reinforced composite root canal post to provide restoration of an endodontically-treated tooth. Grande, et al. use an inlay pattern with patterned resin or polyvinyl siloxane.

SUMMARY OF THE INVENTION

It is an object of the disclosed subject matter to provide a novel method of restoring anterior and posterior endodontically treated teeth.

It is also an object of the disclosed subject matter to provide a method for restoring anterior and posterior endodontically treated teeth wherein the posterior end of a modified porcelain post is positioned in a cement to act as a ferule and prevent microleakage.

It is a further an object of the disclosed subject matter to provide a method for restoring anterior endodontically treated teeth wherein a porcelain veneer is positioned on the labial surface of the tooth, using EMAX™, zirconia, or alumina having properties of great strength and esthetics.

It is a yet further object of the disclosed subject matter to provide a method for restoring anterior endodontically treated teeth wherein a rhomboid shaped porcelain access inlay core is positioned at the access opening with a connected modified porcelain post.

It is a yet further object of the disclosed subject matter to provide a method and apparatus for restoring anterior teeth after endodontic treatment, said method and apparatus comprising:

(1) a formable polymeric member capable of forming a modified post and inlay core impression, with an impression material, such a methyl methacrylate Parkell Relate™ blue burn out resin or other similar impression materials;

(2) a formable polymeric member capable of forming a veneer impression, such as polyvinyl siloxane, PVS, IMPREGUM™ polyether dental impression material, available from 3M, Minneapolis, Minn., or other similar types of impression materials;

(3) cement to prevent microleakage, forming a post barrier, such as MTA or Super EBA or Brassier® Endo™ Sequence Repair Material as well as any suitable cement that prevents the egress of moisture or microleakage to the apex of the root canal;

(4) cement to cement a porcelain modified post and inlay core in position, such as Nexus™ a RelyX™, Ivoclar, or Variolink cement; and (5) bonding cement to cement a porcelain veneer, such as Nexus™ Clear Cement™ or any other light only polymerized cement. The placement of a silane coupling agent is the key to providing a strong chemical bond between the cement and veneer. It is placed on the prepared porcelain restoration.

It is a yet a further object of the disclosed subject matter to provide a method of restoring an anterior tooth after endodontic treatment, comprising:

providing an endodontically treated anterior tooth with chamfer preparations on labial, and incisal, surfaces and a rhomboid shaped opening in the lingual surface extending to a root canal, filled with gutta percha in the root canal;

removing gutta percha from the root canal to provide a post space for a formable polymeric member in the form of a sprue capable of forming a modified post and inlay core impression;

inserting a polymeric plastic sprue (Burn Out Post and Core Pattern), cut to fit the canal loosely to form a DIRECT post pattern. Use appropriate post drills creating a final taper or parallel preparation. Use KY Jelly™ to lubricate canal. Use DURALAY™ (methyl methacrylate or Relate™), monomer and powder, to take an impression of the post space and rhomboid inlay core preparation.

from the impression, preparing a modified post and inlay from one of the EMAX™, zirconia, or alumina porcelains, the finished and inlay core and modified post extension, having an apical end and an occlusal end containing the rhomboid shaped inlay;

forming a post space barrier by injecting a cement to prevent the egress of coronal microleakage. Place about 2 to about 3 mm of MTA, Super EBA cement or Brassier® Root Canal Apico™ cement into the root canal to avoid microleakage;

Use the One Step bonding agent, Prime and Bond, Dentsply™ in the canal and injecting a second cement using Light Only Polymerized Cement, NX3 Cement™ or RelyX™, Ivoclar™, or Variolink™ cement, capable of bonding the modified post and inlay core to the root canal;

inserting the apical end of the modified post and inlay core into the root canal to contact the post barrier cement(s);

smoothing the occlusal end of the modified post and inlay core to be co-extensive with the lingual surface of the tooth;

removing from about 0.2 to about 0.3 mm of enamel from the labial enamel and about 0.2 mm from the incisal surfaces of the tooth to prepare a chamfer to receive the margin outline of the porcelain veneer; The incisal reduction can be used at the practitioner's discretion for labial veneer design.

taking an impression of the veneer preparation using Impregum™ rubber cement or poly vinyl siloxane impression cement using dental impression trays to incorporate the preparation for reproduction;

having a lab prepare a temporary plastic veneer with a selected shade until the final veneer is completed;

cementing with spot cementation on the labial preparation;

pumicing off after temporary plastic veneer is removed and permanent veneers are tried into place;

preparing a porcelain veneer made of zirconia or EMax™ porcelain from the impression of the veneer preparation; and cementing the porcelain veneer into the veneer preparation, by isolating the teeth with rubber dam, the proximals of the tooth with plumber's tape and paper points interproximally.

An anterior tooth is typically treated endodontically by removing the enamel and dentin tooth surfaces, causing a portal in the lingual or occlusal portion of the tooth structure, and removing diseased and/or dead nerve tissue. The root canal is filled with a material such as gutta percha, and sealer. The upper portion of the canal is finished to be smooth with the remaining surface. A temporary veneer may be installed.

Intact endodontically treated anterior teeth do not need complete crown coverage unless they are weakened by large and/or multiple coronal restorations. Use of a porcelain facial veneer restoration with minimally invasive preparation, combined with insertion of an access modified post and inlay core, is an alternative to the natural tooth with a composite access seal or to a metallic post core and crown. It is believed that porcelain veneers, such as EMAX™, zirconia, or alumina porcelain veneers, will support the clinical crown of an anterior endodontically treated tooth to prevent fracturing. Further support from the lingual surface, using the same material, should give additional backing to the clinical crown. The use of minimal veneer preparation along with a very slight lingual wrap minimizes the amount of tooth structure that is removed. The veneer is buttressed by a lingual inlay core/modified post restoration.

According to an embodiment of the disclosed subject matter, about 2 or 3 millimeters below the height of the crest of bone, the gutta percha of the endodontically treated tooth is removed to form a post space to receive a modified porcelain post. An additional about two to about three millimeters of the gutta percha are removed to accommodate the post barrier cement to form a post space barrier. The upper portion of the lingual tooth surface is configured to receive a rhomboid shaped inlay core. A modified porcelain post and inlay core is prepared by a dental laboratory, is fitted for insertion and seal of the access preparation, and is cemented into position. The post space is prepared with a reamer, such as a Brassier® Post Prep Reamers (Post Drills) for post space preparation or Parkell Endodontic Reamers A, B C (Post Drills).

The apical end of the post preparation is round. The post preparation is parallel in design. After being checked for proper insertion and fit, use a bonding agent, such as One Step bonding agent by Dentsply™ in the canal. The walls of the post space, and the post and inlay core, are coated with a light only polymerized cement, such as Nexus™ or RelyX™, Ivoclar™ or Variolink™ cement prior to final insertion for cementation. These cements are beneficial for bonding and preventing microleakage. Cement the Inlay with modified post preparation. Use a curing light, such as a Valo® (Ultradent)™ curing light for 20 seconds or more to allow deep penetration. Remove excess cement from the margins of the inlay, finish and polish.

The modified post and inlay core is cemented into the root space preparation, using a light only polymerized cement, such as Nexus™ or RelyX™, Ivoclar™ or Variolink™. The walls of the post space, and the post and inlay core, are coated with cement prior to final insertion for cementation. These cements are beneficial in preventing microleakage and cementing porcelain restorations.

The core is the material that encircles the post after it emerges from the post space preparation into the coronal portion of the tooth. According to the disclosed subject matter, a post has some core material encircling it inside the crown, with an inlay core seal at the access opening on the lingual side of the tooth. All parts are connected and made of porcelain.

In another aspect of the disclosed subject matter, the labial and incisal surfaces of the tooth are treated to prepare a chamfer to receive a porcelain veneer. After an impression is taken and the veneer is made from the impression, the veneer is cemented to the indentation (chamfer preparation).

According to an embodiment of the disclosed subject matter, a cement is used in the lower portion of the root canal as a barrier to microleakage. This cement also provides a stable anchor ferule for a porcelain fabricated post. The porcelain inlay and post are used to support the facial tooth and veneer.

The modified post and inlay core and the porcelain veneers are sometimes fabricated with the aid of 3-dimensional imaging software. This technology offers esthetics and an immediate fabrication of the selected EMAX™, zirconia porcelains anterior tooth.

More particularly, the procedures according to the disclosed subject matter combine existing imaging and fabrication technologies and cements in a novel procedure to restore anterior teeth after root canal. Reproduction of veneers and inlay core with modified post can also be fabricated by using the IPS emax Ceram layering ceramic and other porcelain materials techniques.

The disclosed subject matter may be better implemented with the development of advanced scanning probes that can scan into the root canal. Such scanning probes would be thin enough to scan the inlay core and post preparation. A very thin probe should be developed to capture the image of the post preparation in the root canal space, along with development of software that can read the scans taken and reproduce them in porcelain cutting machines. This will enable the reproduction of the post/inlay core with hardware provided for porcelain reproduction in the office. It would not be necessary to send materials to a laboratory for a direct cast reproduction, resulting in a savings of time and money.

Overall, the technology disclosed herein is less invasive and requires the removal of less tooth structure than current technology for restoring anterior teeth after endodontic treatment.

The instant technique includes:
injecting a cement barrier, for example, of from about 2 to about 3 mm of MTA, Super EBA, or Brassier® Root Canal Apico™ Cement into the root canal to prevent microleakage;
injecting a second cement capable of bonding the modified post and inlay core to the root canal, such as light only polymerized cement, such as Nexus™ RelyX™, Ivoclar™, or Variolink™ cement;
inserting the apical end of the modified post and inlay core into the root canal to contact the post barrier cement;
smoothing the occlusal end of the modified post and inlay core to be co-extensive with the lingual surface of the tooth;
removing from about 0.2 to about 0.3 mm of enamel from the labial and about 0.2 mm from the incisal surfaces or less of the tooth to prepare a chamfer to receive the margin outline of the porcelain veneer;
taking an impression of the veneer preparation;
having a lab prepare a temporary plastic veneer with a selected shade until the final veneer is completed;
cementing with spot cementation on the labial preparation;
pumicing off after temporary plastic veneer is removed and permanent veneers are tried into place;
preparing a porcelain veneer from the impression of the veneer preparation; and
cementing the porcelain veneer into the veneer preparation, by isolating with rubber dam, and placing plumber's tape and paper points interproximally.

In one aspect of the disclosed subject matter, a basic tray for the porcelain veneer, comprises a Brasseler® Laminate Burs Kit™, Diamond Chamfer Burs, vacuum-formed stent for transportation of putty index, VPS light body and medium body material, Impregum™, poly vinyl siloxane impression cement, to take an impression using dental impression trays to incorporate the preparation for reproduction. Order a lab preparation with the taken impression to construct a labial veneer with EMAX™, zirconia, or alumina.

In another aspect for delivery, a basic tray comprises One Step bonding agent, Prime and Bond by Dentsply™ on the facial veneer preparation, etching the porcelain veneer with 9.6% hydrofluoric acid, using highly filled flowable resin or a conventional resin composite cement to cement the veneer. The placement of a silane coupling agent is the key to providing a strong chemical bond between the cement and veneer. Place it on the prepared porcelain. Follow the manufacturer's recommendation for length of time placement of the silane. Use resin cement to cement the veneers anterior and posterior post/inlay Light Cure Type Nexus™, Vario Link™ finishing burs (Brasseler Laminate Burs Kit), and interproximal serrated strips.

While the technology disclosed and described herein primarily pertains to the treatment of anterior endodontically treated teeth, the principles here are also applicable to the treatment of posterior endodontically treated teeth.

These and other objects and advantages of the present invention are more readily apparent with reference to the following detailed description and the accompanying drawings.

In accordance with the present invention, there is provided a restored anterior teeth/endodontic veneer after endodontic treatment. A ceramic porcelain material is provided that, after being formed from a CAD scan or impression, aids in fabricating a labial porcelain veneer and a rhomboid lingual access inlay of the porcelain material with an anatomical post extension connected thereto. A cement material is provided for preventing microleakage into gutta percha and for forming a post-barrier space. A porcelain inlay-shaped core is provided comprising an anatomical post extension extending from a level of an existing crest of bone of a patient into a root canal space, the length of the post extension being less than one-half the length of a root canal.

BRIEF DESCRIPTION OF THE DRAWINGS

A complete understanding of the present invention may be obtained by reference to the accompanying drawings, when considered in conjunction with the subsequent detailed description, in which:

FIG. 1 is a cross-sectional view of an anterior tooth that has been endodontically treated;

FIG. 2 is a cross-sectional view of the tooth in FIG. 1 where the tooth has been prepared to take an impression;

FIG. 6 is a top view of the tooth of FIG. 4;

FIG. 7 is another top view of the tooth of FIG. 4;

Like reference numerals refer to like parts throughout the several views of the drawings.

DETAILED DESCRIPTION OF THE PREFERRED EMBODIMENT

Figure 3:
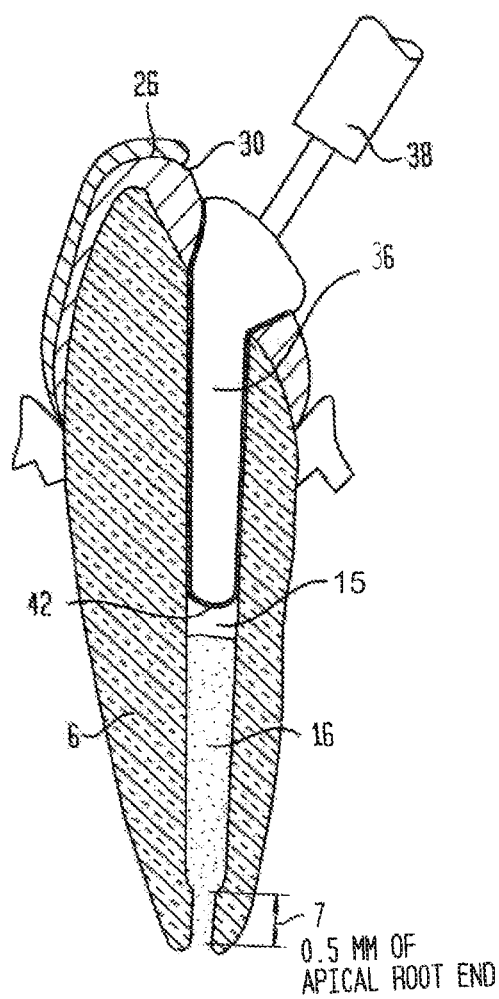
FIG. 3 is a cross-sectional view of the tooth in FIG. 2 where an impression is being taken for the post and inlay core.

Although the following detailed description contains specific details for the purposes of illustration, those of ordinary skill in the art will appreciate that variations and alterations to the following details are within the scope of the invention. Accordingly, the exemplary embodiments of the invention described below are set forth without any loss of generality to, and without imposing limitations upon, the invention.

Restored anterior teeth/endodontic veneer after endodontic treatment has a ceramic porcelain material that, after being formed from a CAD scan or impression, provides dimensional characteristics for fabricating a labial porcelain veneer and a rhomboid lingual access inlay of the porcelain material with an anatomical post extension connected thereto. A cement material is provided for preventing microleakage into gutta percha and for forming a post-barrier space.

The preferred embodiments of the disclosed subject matter will now be described with reference to the drawings. Identical elements in the various figures are designated with the same reference numerals.

FIG. 1 illustrates a cross-sectional view of an endodontically prepared anterior tooth prior to further processing. A tooth has a crown 8 and a root 17. Crown 8 comprises enamel 10 and dentin 12. The tooth has a root canal 20 and a rhomboid shaped access 1 to the root canal 20, forming a root canal prep space 18 that are filled with gutta percha 16 and cement, such as Columbia cement.

In the cross-sectional view of FIG. 2, cement and a calibrated amount of gutta percha 16 has been removed from a root canal prep space 18. An indentation chamfer preparation of 0.3-05 mm has been created in enamel 10 on a labial surface 24 and an incisal surface 26, to a depth of from about 0.3 mm to about 0.5 mm. The upper edge 30 of indentation 22 ends approximately about 2 mm to about 3 mm from the upper edge 32 of cavity 20.

A formable polymeric member 36, formed from a methyl methacrylate, which has a sprue 38, is lubricated with a DURALAY™ Tin Lubricant, a petroleum-based lubricant product such as Vaseline® petroleum jelly, or a glycerin based lubricant, such as K-Y™ jelly and then inserted into cavity opening 20 and root canal prep space 18, as shown in FIG. 3. The formable polymeric member impression material 36 is withdrawn slowly and reinserted to prevent permanent locking. Once polymeric member methyl methacylate 36 hardens, it is used to form a modified post and rhomboid shaped access inlay core 52 in a separate step. In one aspect of the invention, a modified post and rhomboid shaped inlay core 52 is prepared scanning the impression, and using CEREC 3-D software, as described herein below.

The apical end 42 of polymeric member 36 and sprue 38 is positioned (for example, by X-ray) about 2 mm to about 3 mm below the cervical portion of the tooth (gingival margin 9) between enamel and root cementum 6. There is a gap, the post barrier space 15, in root canal of about 2 mm for the post barrier cement 51, made up of MTA™ and Super EBA™. This space 15 lies directly below the terminus 42 of the prepared polymeric membrane post 36 which lies 1.5 mm into the post barrier cement 51, creating a second ferule. The post barrier space 15 lies between apical end 42 of the polymeric member 36 and the remaining filled gutta percha 16, which is more than 4 mm in length.

A formable member (not shown) is also used to form an endodontic veneer 4, such as Endodontic Veneer EV™, from the chamfer indentation 22 on the enamel 10. The final Endodontic Veneer EV™, a porcelain veneer 4, receives lingual support from the rhomboid shaped access 1 on the lingual and cast core with post extension 52.

CEREC 3-D software or scanning can reproduce the Endodontic Veneer EV™ 4 and rhomboid access 1 with inlay shaped walls 11, and attached post extension. 52. FIG. 3 shows a cross-sectional view of the tooth in FIG. 2 where an impression is being taken.

Figure 4:
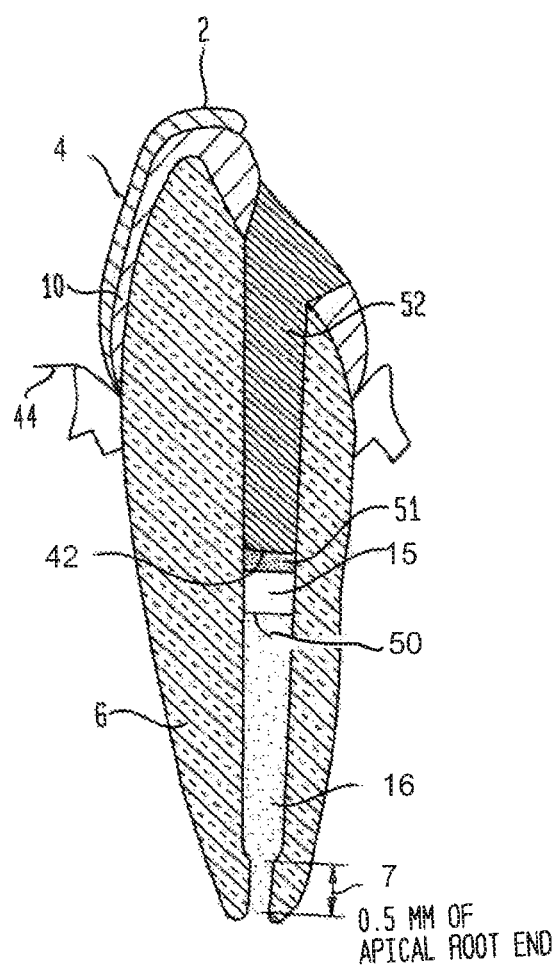
FIG. 4 is a cross-sectional view of the tooth of FIG. 3 where the modified post and inlay core and the veneer inlay have been inserted.
Figure 5:
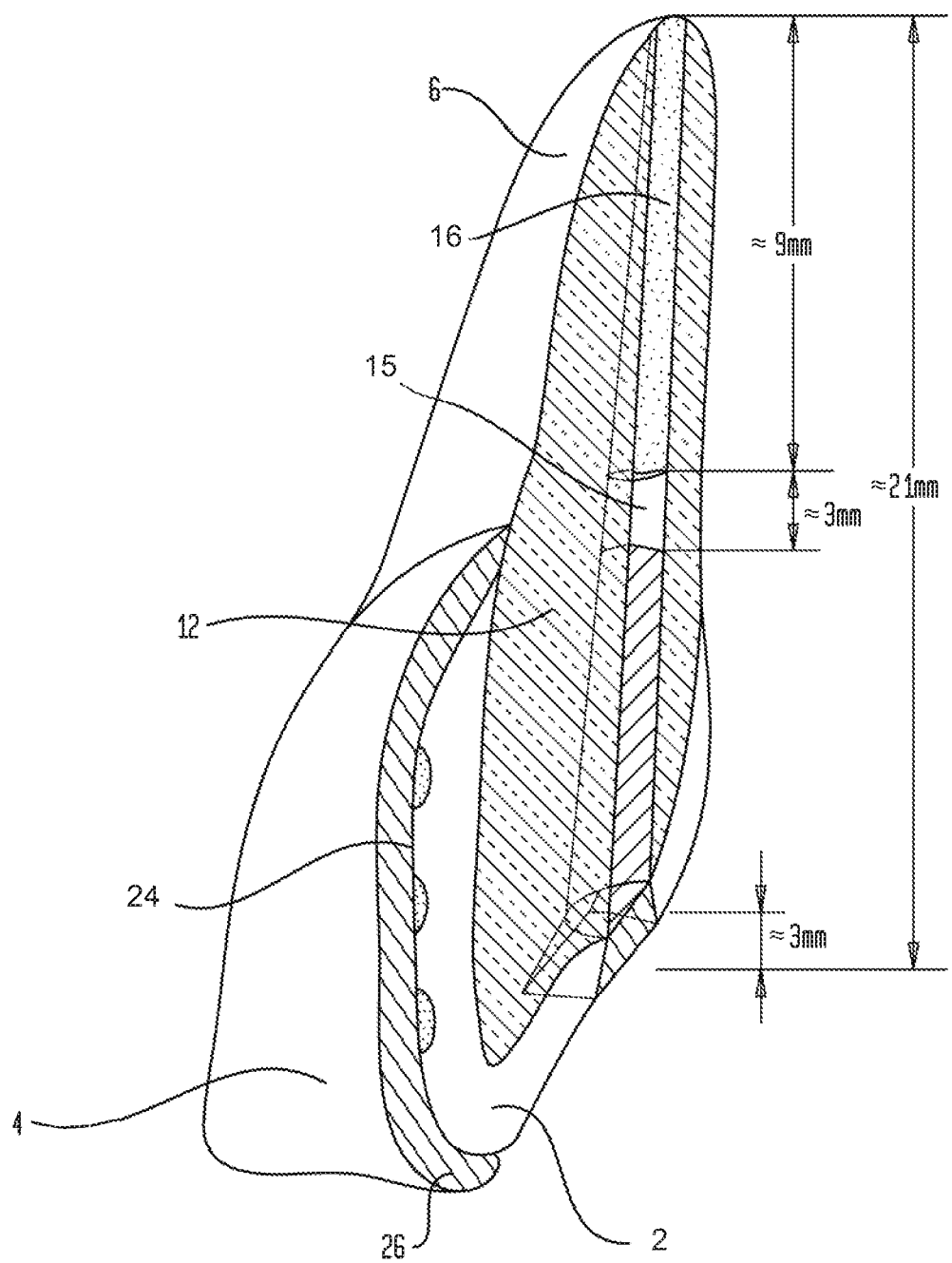
FIG. 5 is another cross-sectional view of the tooth of FIG. 4.
Figure 8:
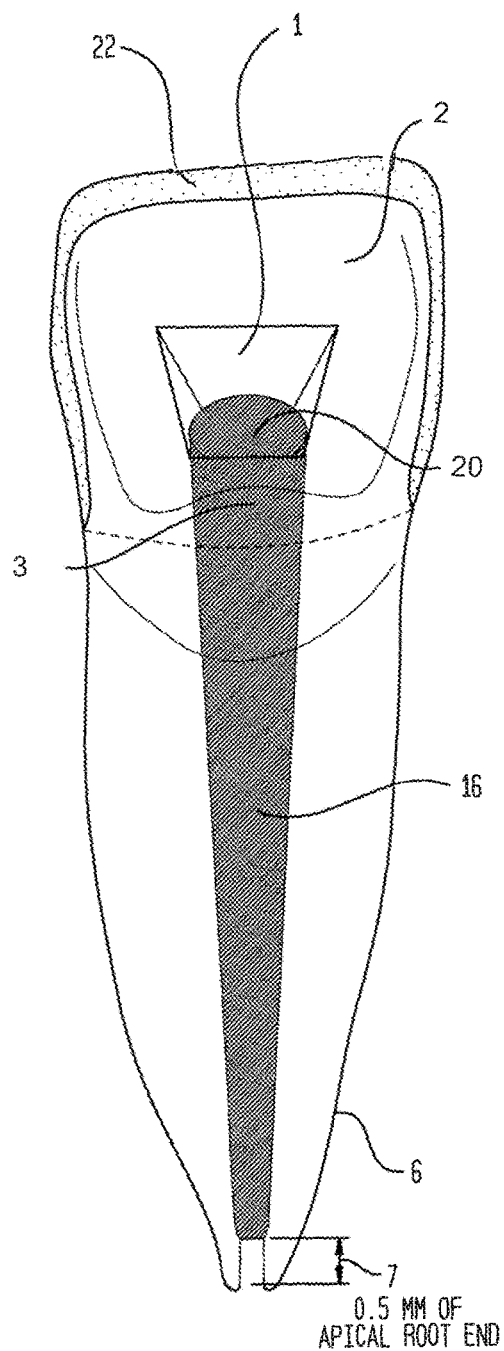
FIG. 8 is a lingual view of the tooth.
Figure 9:
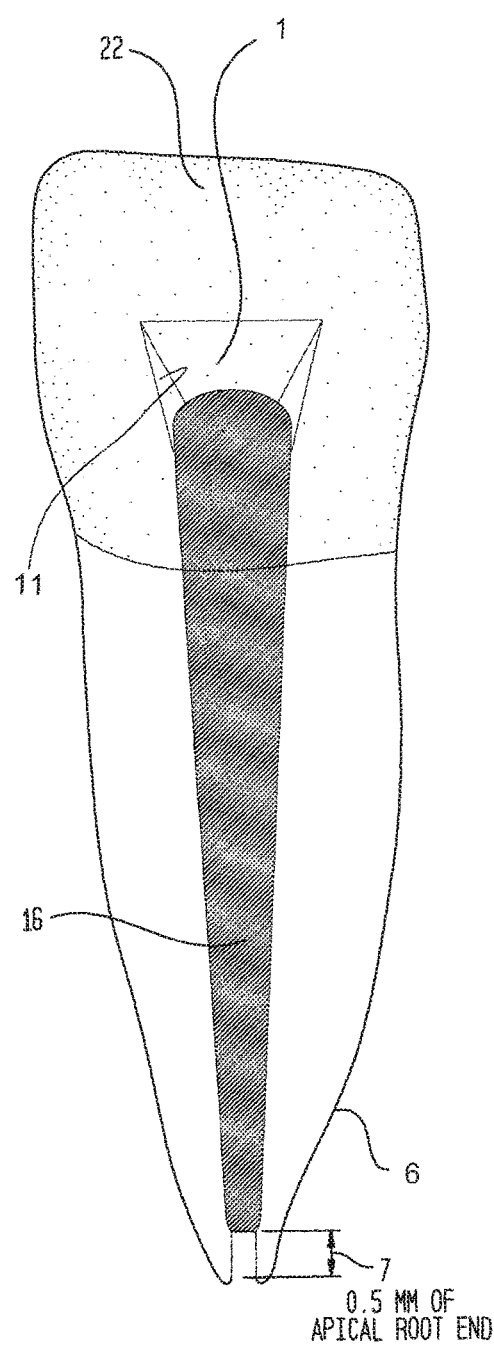
FIG. 9 is a labial view of the tooth.

FIG. 4 shows a cross-sectional view of the tooth of FIG. 3 where the modified post extension and core 52 with post space barrier space 15 are illustrated. To prepare a final tooth according to the disclosed subject matter, as seen in reference to FIG. 4, a post barrier cement 51 to prevent microleakage is injected or inserted into the 2-3 mm open post barrier space 15 proximal to the filled gutta percha 16 in the root canal prep space 18, as shown in FIG. 2. Proximal to the post barrier cement 51 a modified post and rhomboid access shaped inlay core 52 has been cemented into root canal prep space 18, the post 52 being 3-5 mm below the height of the crest of bone 44 and not greater than one half the length of root canal prep space 18. Also, an Endodontic Veneer EV™ 4 has been cemented into labial chamfer 24 (indentation) in the enamel 10.

The facial and incisal surfaces of the teeth are prepared minimally into enamel 0.2 mm-0.3 mm and the rhomboid access opening 1 for the root canal, connected with an inlay shaped core preparation 52 with an extended cast post preparation made of the same materials. The lingual access and cast core and post 52 give additional support to the clinical crown 8 and prevent fracturing. The modified post 52 is seated into a post barrier space 15 filled with post barrier cement, such as Super EBA™, MTA™, Brassier® Root Canal Apico Cement™, or any suitable cement that prevents the egress of moisture or bacterial microleakage to the apex of the root canal.

According to the disclosed subject matter, the extended post and rhomboid access inlay shaped core 52, the labial Endodontic Veneer EV™ 4 are prepared from very strong porcelain, preferably EMAX™, zirconia, or alumina porcelain. This porcelain can comprise zirconia dioxide, ytrium oxide, and cerium oxide. Other suitable porcelain materials such as IPS emax Ceram layering ceramic can also be used.

Various cements are useful according to the disclosed subject matter. A particularly important cement is the one that is injected into the root canal space apical to the terminus of the modified porcelain post to prevent the egress of moisture, 14 that is, bacterial microleakage, into the root canal. Suitable cements for this purpose include Super EBA™ available from Bosworth or mineral trioxide aggregate (MTA),™ available from Dentsply™ and Brassier® Root Canal Apico™ cement. Other cements that prevent the egress of moisture or microleakage can be substituted. These cements have been clinically proven to be successful apical sealers in apicoectomy surgical procedures. Prior to cementation, the post space barrier cement 51 is inserted into the root canal space with a syringe. Any suitable carrier can also be substituted to place the cement barrier into the root canal.

Other cements or bonding agents are useful to cement the modified post and inlay 1 include, but are not limited to, Light Only Polymerized Cement, Nexus and RelyX (from 3M), Ivoclar™, and Variolink™.

Preparation of the indentation for the Endodontic Veneer Ev™ 4 is preferably accomplished with diamond Brasseler® depth cutting burs. The burs are applied to the labial (front surface) 24 and incisal surfaces 2 of an anterior tooth to prepare a reduction of enamel 10 that is uniformly from about 0.3 to about 0.5 mm deep on the labial surface 24 and about 0.3 or less deep on the incisal surface 2. This allows space for the porcelain veneers 4. Caution must be applied not to cut through to the enamel surface of the tooth. A sharply demarcated chamfer (edge or groove) is prepared on the proximals, gingival margin 9, and at the terminus of the incisal preparation on the lingual side of the tooth. This permits the wraparound of the porcelain veneer 4 over the incisal to the lingual side of the tooth. The incisal 2 may not have to be prepared with a wraparound of the labial porcelain veneer 4. The edge or groove (chamfer) 26 defines the enamel reduction.

The Endodontic Veneer EV™ 4 is prepared from PVS (polyvinyl siloxane) impressions of the tooth. This impression is sent to a dental laboratory to prepare the temporary and final veneers. Teeth may be left uncovered or covered with temporary veneer restorations until the final veneer has been fabricated. The final porcelain veneer 4, Endodontic Veneer EV™, can also be formed in the dental office from a hard solid porcelain block using three-dimensional software, CEREC, an acronym for Chair side Economical Restoration of Esthetic Ceramics, such as described above. The prepared tooth can be restored in a single visit appointment with no need to construct temporaries or have lab fees.

As described hereinabove, a ceramic porcelain material is introduced that, after being formed from a CAD scan or impression, aids in fabricating a labial porcelain veneer 4 and a rhomboid lingual access inlay shaped core with an anatomical post extension 52 connected thereto. A Brassier® reamer or Parkell C-1 reamer is used to remove gutta percha 16. Additional gutta percha 16 is removed for placing a post barrier space 15 with cement 51 comprising MTA or Super EBA cement 14.

Approximately 2-3 mm of gutta percha 16 below the height of the crest 44 of existing bone, are initially removed for post space preparation and an additional 2 mm of gutta percha 16 are removed for the Super EBA™, Brassier® Endo Sequence Repair Material™ as post barrier material 51. The post space barrier cement 51 is inserted into the root canal space prior to cementation with a syringe and the ceramic porcelain facial veneer 4 and porcelain inlay with modified post 52 are cemented using Rely X™ Ivoclar™ or Variolink Cement™. The modified post 52 is placed to imprint itself into the barrier cement material 51, forming a secondary ferrule which prevents dislodging of the post 52.

In preparing the modified post space 15, use a parallel sided or a tapered depth preparation creating a parallel sided or parallel preparation. The space 15 is lubricated with a petroleum jelly or lubricant, such as K-Y jelly, Duralay lubricant DURALAY™ polyacrylic resin, available from Reliance Dental Mfg. Co., of Alsip, Ill. A plastic sprue 38 (Burn out Post and Core Pattern or Relate™ Blue Burn Out Resin) is cut to fit the canal loosely and adjust to a length 2 mm short of contact with said gutta percha 16 to form a direct post pattern. Half fill the canal with methyl methacrylate 36 or Relate™ Parkell blue burn out resin (which will have the consistency of a soupy mix). Use a brush dip Nelon technique to add the methyl methacrylate 36 or Relate™ burn out sprue 38 after it has been made wet with a monomer. Insert the sprue 38 into the post space and move in and out to avoid locking. The impression material 36 is extended to cover the inlay core preparation 1, filling in all margins of the tooth. After completely set, withdraw the sprue 38 and send to a laboratory to fabricate the porcelain inlay shaped core with a post extension 52.

An impression is taken using poly vinyl siloxane or Imregum Cement™ of the chamfer preparation of the enamel 10 for forming a ceramic Endodontic Veneer EV™ 4. Using a porcelain selection of EMAX™, zirconia, or alumina porcelain, Light Only Polymerized Cement or any other similar type to form the veneer 4. Upon completion, the veneer 4 is cemented on to the prepared tooth surface using Nexus Clear™, or any other type of light only polymerized cement.

As described hereinabove, a polymeric form (sprue) 38 is inserted into the root canal to form an impression to be used to prepare the modified post and rhomboidal inlay core 52. There are a number of polymeric materials that are known to be useful for this purpose. A preferred material is DURALAY™ polyacrylic resin, available from Reliance Dental Mfg. Co., of Alsip, Ill. Another material is Parkell Relate™ Blue Burn Out Resin.

A Study Applying the Invention to Extracted Human and Plastic Model Teeth

The purpose of a study was to construct an alternative model restoration for an anterior endodontically treated tooth with Endodontic Veneer EV™. By constructing a minimal veneer preparation of about 0.5 mm or less, the intent was to reduce the amount of tooth structure and restore it with a strong porcelain veneer 4. The veneer 4 would be buttressed by a lingual, rhomboidal shaped inlay core/with extended post 52 restoration to prevent the shearing of the clinical crown 8 at the cervical interface.

Materials and Method:

A total of twenty-four root canal treated anterior teeth were instrumented, filled with gutta percha 16 and sealer, and prepared minimally for facial veneers 4. Gutta percha 16 was removed from the root canal space to allow for modified post placement and post space barrier. A post space preparation was made using a Brasseler® Para Post non-end cutting, domed shaped peezo Bur™. Super EBA cement and MTA cement were used as the post space barrier material 51. Previous microleakage studies showed these materials to be resistant to the penetration of microleakage.

Of the twenty-four teeth, sixteen teeth were plastic typodont, and eight were extracted human anterior teeth. Brasseler® depth cut Burs™ were used to remain in enamel 10 and reduce only enough tooth structure so that approximately 0.3-0.5 mm of labial enamel and 0.5 mm of incisal enamel was removed. Twenty-four teeth were prepared for a rhomboid access inlay shaped core 1 with a modified post extension 52 of approximately 3 mm A pattern of the inlay core 1 and modified post 52 was constructed from DURALAY™ poly acrylic. Three zirconia-like modified post and rhomboid access with inlay shaped core restorations were fabricated directly, each tooth using CEREC 3-D Software, which is WINDOWS®-based and three-dimensional. Unlike other restorative methods, this procedure provides maximum control and vision, allowing views of the preparation from all angles. The CEREC 3-D software is available from Sirona Dental Systems.

According to MobileTekLabs, the procedure for constructing a porcelain facial veneer 4 with the CEREC 3-D software is as follows:

Step 1: Start a new restoration.

Step 2: Choose Veneer mode (an anterior tooth must be chosen in order to utilize Veneer mode).

Step 3: Powder the cavity of the tooth.

Step 4: Take an unobstructed image of the cavity; press the green arrow.

Step 5: There is no need to trim the image; press the green arrow.

Step 6: Mark the margin; press the green arrow.

Step 7: A veneer outlined in green will appear. The green outline needs to be the same shape as the margin. Adjust the green line incrementally until it is the same shape as the margin 9. The final shape needs to be slightly smaller in diameter then the margin 9; press the green arrow.

Step 8: Use the form tool to apply 1 mm of material to the surface of the restoration. (This will ensure the sprue 38 is placed in an optimal position.) Press the green arrow.

Step 9: Mill the restoration.

Six porcelain facial veneers were constructed from the CEREC 3D software.

In another procedure, the DURALAY™ impression of the inlay core and modified post impression 36 is sent to a lab where an E Max Porcelain casting can be made and the porcelain reproduction returned for cementation.

Three millimeters of gutta-percha 16 were removed for the post space 15 preparation, and an additional 2 mm were removed for the Super EBA post barrier material 51. MTA cement was also used as a barrier cement material 51.

The porcelain facial veneer 4 and porcelain inlay core with modified post 52 were cemented using Ivoclar or Variolink cement. Any suitable cement for veneer cementation can be substituted. The modified post 52 is placed to imprint itself into the barrier material 51. This procedure can be checked with a radiograph prior to final cementation.

RESULTS AND CONCLUSIONS

Although stress tests were not conducted in this study, a review of the literature would support the use of zirconia-like porcelain veneers 4 to be a useful alternative in restoring endodontically treated teeth. Zirconia exhibits superior strength as a restorative material lends itself to be used without removing excess tooth structure. The replacement of cast and prefabricated metal posts, which lead to micro fractures and failures with zirconia-like porcelain is a plausible alternative. This is a first time presentation of using porcelain facial veneer restorations supported by a lingual inlay core and modified post 52 with endodontically treated teeth. A similar application to this procedure can be applied to posterior teeth with the rhomboid access, inlay shaped core/modified post extension on the occlusal access preparation of endodontically treated teeth.

While various descriptions of the present invention are described above, it should be understood that the various features can be used singly or in any combination thereof. Therefore, the invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. All such modifications, variations and other uses and applications which do not depart from the spirit and scope of the invention are deemed to be covered by the invention, which is defined as set forth in the claims which follow.

Since other modifications and changes varied to fit particular operating requirements and environments will be apparent to those skilled in the art, the invention is not considered limited to the example chosen for purposes of disclosure and covers all changes and modifications which do not constitute departures from the true spirit and scope of this invention.

Having thus described the invention, what is desired to be protected by Letters Patent is presented in the subsequently appended claims.

What is claimed is:

1. A method of restoring an anterior endodontically treated tooth, having labial, incisal, and lingual surfaces, said method comprising: forming a root canal space and a rhomboid access inlay in the lingual surface of the tooth, the rhomboid access inlay having converging sidewalk extending into the root canal space; forming a veneer surface preparation on the labial surface of the tooth;
   forming an anatomical model of the root canal space and the rhomboid access inlay with one of a CAD scan Or an impression material;
   using a reamer to remove endodontic treatment material from the root canal space,
   forming an anatomical veneer model of the veneer surface preparation with one of a CAD scan or a veneer impression material;
   and fabricating a porcelain rhomboidal inlay core with a post extension pursuant to said anatomical model,
   cementing said porcelain rhomboidal inlay core into the space of said rhomboid access inlay,
   and cementing said porcelain veneer onto said veneer surface preparation.

2. The method of claim 1, wherein said porcelain rhomboidal inlay core with post extension has an apical end and an occlusal end.

3. The method of claim 2, further comprising:
   injecting a portion of a cement into the root canal space to form a post barrier to prevent micro leakage.

4. The method of claim 3, further comprising:
   injecting a portion of an adhesive cement into the root canal space capable of bonding the apical end of the rhomboid inlay core with post extension to the root canal space.

5. The method of claim 4, further comprising
   inserting the apical end of the post extension into the root canal space to contact 1.5 mm of the post barrier.

6. The method of claim 1, further comprising:
   smoothing the occlusal end of the rhomboidal inlay core to be co-extensive with the lingual surface of the tooth.

7. The method of claim 1, wherein forming the veneer surface preparation comprises:
   removing 0.5 mm of the labial and incisal surfaces to create a chamfer to receive a margin outline of the endodontic porcelain veneer.

8. The method of claim 7, further comprising:
   preparing a temporary plastic veneer with a selected shade until a final veneer is completed.

9. The method of claim 8, further comprising cementing the temporary veneer with a spot cementation on the labial veneer surface preparation.

10. The method of claim 9, further comprising:
pumicing off the veneer surface preparation after a temporary plastic veneer is removed and a permanent porcelain endodontic veneer is tried into place.

11. The method of claim 1, further comprising preparing a ceramic porcelain endodontic veneer from the anatomical veneer model.

12. The method of claim 11, further comprising cementing the ceramic porcelain veneer onto the veneer surface preparation.

13. The method of claim 1, wherein said impression material comprises methyl methacrylate.

14. The method of claim 7, wherein forming the modified veneer surface preparation further comprises:
preparing a chamfer by removing from about 0.2 to about 0.3 mm of enamel from the labial surface of the tooth and about 0.2 mm from the incisal surface of the tooth.

15. The method of claim 1, wherein said ceramic porcelain endodontic veneer is cemented into the modified veneer surface preparation by isolating the proximal portion of the tooth with plumber's tape and paper points interproximally.

16. A method for restoring anterior teeth/endodontic veneer after endodontic treatment, the method comprising:
 a) creating a root canal space with a lingual rhomboid access inlay preparation opening into the root canal space;
 b) cleaning and shaping said root canal space to 0.5 mm of apical root end, said root canal space being tapered to allow a sodium hyperchloride irrigation to reach an apical area;
 c) fitting gutta percha to said root canal space and filling said root canal space with a root canal sealer comprising zinc oxide eugenol sealer with gutta percha using lateral-vertical condensation;
 d) removing a portion of said gutta percha using a burr up to 3 mm less than ½ of root length for a post space and an additional 2 mm for a post barrier space;
 e) fitting a plastic sprue within the root canal space, leaving space for a polymeric resin material to form to said root canal space;
 f) roughening a surface of the plastic sprue; to have the polymeric resin adhere;
 g) measuring said sprue for position, length, and within said root canal space;
 h) adjusting said sprue to accommodate proper draw for forming an anatomical impression pattern;
 i) mixing the polymeric resin material;
 j) introducing said polymeric resin material into said lingual rhomboid access inlay shaped core and said post space with said sprue;
 k) forming said polymeric resin to said lingual rhomboid access inlay shaped core and said post space to form the anatomical impression and inserting said sprue therein;
 l) withdrawing said anatomical impression;
 m) fabricating a porcelain rhomboid shaped inlay core with post extension restoration from said anatomical impression by using one of a laboratory and a CEREC machine;
 n) fitting said porcelain rhomboid shaped inlay core with said post extension to the lingual rhomboid access inlay shaped core preparation and the root canal space;
 o) applying a cement into said root canal space; and
 p) inserting said restoration into said root canal space and rhomboid access inlay.

* * * * *